US012090180B2

(12) United States Patent
Mani et al.

(10) Patent No.: US 12,090,180 B2
(45) Date of Patent: *Sep. 17, 2024

(54) MICROBIAL HYPERSWARMERS AND USES THEREOF

(71) Applicant: Albert Einstein College of Medicine, Bronx, NY (US)

(72) Inventors: Sridhar Mani, Riverdale, NY (US); Libusha Kelly, Brooklyn, NY (US); Hao Li, Elmsford, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 356 days.

This patent is subject to a terminal disclaimer.

(21) Appl. No.: 17/496,919

(22) Filed: Oct. 8, 2021

(65) Prior Publication Data

US 2022/0080002 A1    Mar. 17, 2022

Related U.S. Application Data

(60) Continuation of application No. 17/017,105, filed on Sep. 10, 2020, now Pat. No. 11,141,441, which is a division of application No. 15/765,513, filed as application No. PCT/US2016/052742 on Sep. 21, 2016, now Pat. No. 10,857,190.

(60) Provisional application No. 62/237,657, filed on Oct. 6, 2015.

(51) Int. Cl.
| | |
|---|---|
| *A61K 35/744* | (2015.01) |
| *A61K 9/00* | (2006.01) |
| *A61K 9/48* | (2006.01) |
| *A61K 35/741* | (2015.01) |
| *A61K 35/742* | (2015.01) |
| *A61P 1/14* | (2006.01) |
| *C12N 1/20* | (2006.01) |
| *G01N 33/483* | (2006.01) |

(52) U.S. Cl.
CPC ............. *A61K 35/744* (2013.01); *A61K 9/48* (2013.01); *A61K 35/741* (2013.01); *A61K 35/742* (2013.01); *C12N 1/20* (2013.01); *G01N 33/483* (2013.01); *A61K 9/0031* (2013.01); *A61K 9/0053* (2013.01); *A61P 1/14* (2018.01); *Y02A 50/30* (2018.01)

(58) Field of Classification Search
CPC ...... A61K 35/744; A61K 9/48; A61K 35/741; A61K 35/742; A61K 9/0031; A61K 9/0053; C12N 1/20; G01N 33/483; A61P 1/14; Y02A 50/30
See application file for complete search history.

(56) References Cited

U.S. PATENT DOCUMENTS

| | | | |
|---|---|---|---|
| 9,925,222 B2 | 3/2018 | Mani et al. | |
| 10,857,190 B2 * | 12/2020 | Mani | A61K 35/744 |
| 2008/0057047 A1 | 3/2008 | Sas et al. | |
| 2009/0148389 A1 | 6/2009 | Rottiers et al. | |
| 2013/0004540 A1 | 1/2013 | O'mahony et al. | |
| 2013/0101566 A1 | 4/2013 | Espadaler Mazo et al. | |

FOREIGN PATENT DOCUMENTS

WO    2004093909 A1    11/2004

OTHER PUBLICATIONS

Gardel and Mekalanos. "Alterations in Vibrio cholerae motility phenotypes correlate with changes in virulence factor expression." Infection and immunity 64.6 (1996): 2246-2255 (Year: 1996).*
Van Ditmarsch, et al. "Convergent evolution of hyperswarming leads to impaired biofilm formation in pathogenic bacteria." Cell reports 4.4 (2013): 697-708 (Year: 2013).*
Deforet et al. "Hyperswarming adaptations in a bacterium improve collective motility without enhancing single cell motility." Soft matter 10.14 (2014): 2405-2413 (Year: 2014).*
Morales-Soto et al. "Preparation, imaging, and quantification of bacterial surface motility assays." JoVE: Journal of Visualized Experiments, 98 (2015): e52338 (Year: 2015).*
PCT International Search Report and Written Opinion dated Feb. 7, 2017 for PCT International Patent Application No. PCT/US2016/52742, 10 pages.
Van Ditmarsch D et al., Convergent Evolution of Hyperswarming Leads to Impaired Biofilm Formation in Pathogenic Bacteria, Cell Reports, Aug. 29, 2013, vol. 4, No. 4, pp. 697-708.
Ones S E et al., Protection from Intestinal Inflammation by bacterial exopolysaccharides, Journal of Immunology, May 15, 2014, vol. 192, No. 10, pp. 4813-4820.
Deforet, M., et al. "Hyperswarming adaptations in a bacterium improve collective motility without enhancing single cell motility" Soft Matter, vol. 10, pp. 2405-2413, 2014.
Gardel et al. "Alterations in Vibrio cholerae Vlotility Phenotypes Correlate with Changes in Virulence Factor Expression", Infection and Immunity, 64(6):2246-2255, Jun. 1996.

* cited by examiner

*Primary Examiner* — Aaron J Kosar
*Assistant Examiner* — Andrew T Moehlman
(74) *Attorney, Agent, or Firm* — Fox Rothschild LLP

(57) ABSTRACT

Bacterial hyperswarmers are disclosed for treatment, prevention and diagnosis of conditions such as intestinal inflammation.

5 Claims, 14 Drawing Sheets

|  | average coverage | length (bp) | genes |
|---|---|---|---|
| Strain 1 | 142 | 4883160 | 4534 |
| Strain 2 | 154 | 4886296 | 4507 |
| Strain 3 | 115 | 4881044 | 4510 |

MICROBIAL HYPERSWARMERS AND USES THEREOF

CROSS-REFERENCE TO RELATED APPLICATION

This application is a divisional of U.S. patent application Ser. No. 15/765,513, filed Apr. 3, 2018, which is a U.S. national stage entry under 35 U.S.C. § 371 of PCT International Patent Application No. PCT/US2016/052742, filed Sep. 21, 2016, which claims the benefit of U.S. Provisional Patent Application No. 62/237,657, filed Oct. 6, 2015, the contents of each of which are herein incorporated herein by reference.

STATEMENT OF GOVERNMENT SUPPORT

This invention was made with government support under grant number CA161879 awarded by the National Institutes of Health. The government has certain rights in the invention.

BACKGROUND OF THE INVENTION

Throughout this application various publications are referred to in superscripts. Full citations for these references may be found at the end of the specification before the claims. The disclosures of these publications are hereby incorporated by reference in their entireties into the subject application to more fully describe the art to which the subject application pertains.

Bacterial swarming is a unique, conserved and distinct bacterial motility property. Swarming, driven by flagella, is a fundamental process in bacteria allowing for rapid movement across a surface[1,2]. Swarming motility is often oppositely regulated and antagonistic to biofilm formation[1,2]. To date, while bacterial biofilms have been associated with pathogenesis and/or pathobiology of human diseases (e.g., infections, inflammation and cancer)[3-6], there are very few examples of swarming behaviors that uniquely define or align with human pathophysiology (e.g., antibiotic resistance)[7]. Indeed, these examples uniformly define bacterial swarming as a pathologic even[8,9]. Swarming offers bacteria a competitive advantage in occupying certain niches[13]. There are discrete examples proposed in which bacterial swarms lead to improved benefits for the entire bacterial community as a whole (e.g., antibiotic resistance); however, cost-benefits to the host surface or environment are essentially unknown[14]. In mammals, the extent to which commensal bacteria swarm and whether this phenotype has any consequence in health and disease are unknown.

Gastrointestinal diseases in farm animals are common, debilitating and in some cases fatal health problems. Most ailments (e.g., viral enteritis) have no known treatments or cures. There has been increasing recognition for use of probiotics in farm animals; however, all the current strains are cocktails based entirely on empiric observations of trial and error.

The present invention uses bacterial hyperswarmers to address the need for methods of treatment, prevention and diagnosis of conditions such as intestinal inflammation.

SUMMARY OF THE INVENTION

Methods are provided for treating and preventing intestinal inflammations in a subject comprising administering to the gastrointestinal tract of the subject bacterial hyperswarmers in an amount effective to treat or prevent an intestinal inflammation in a subject.

Methods are also provided for isolating a bacterial strain for treating an intestinal inflammation from a complex bacterial mix, the methods comprising isolating bacterial hyperswarmers as a single bacterial strain from fecal material on a plate agar assay under aerobic conditions and propagating the bacterial hyperswarmers in culture.

Methods are also provided for diagnosing an intestinal inflammation in a subject, the methods comprising culturing bacteria from a fecal sample from the subject under aerobic conditions, and examining the culture for the presence of bacterial hyperswarmers, where bacterial hyperswarmer are identified as bursts emanating from the edge of a bacterial swarming colony, and where the presence of bacterial hyperswarmers in a fecal sample from a subject is indicative that the subject has an intestinal inflammation.

Composition are provided for treating an intestinal inflammation in a subject, where the compositions comprise bacterial hyperswarmers in an amount effective to treat an intestinal inflammation.

DETAILED DESCRIPTION OF THE INVENTION

Figure 1A:
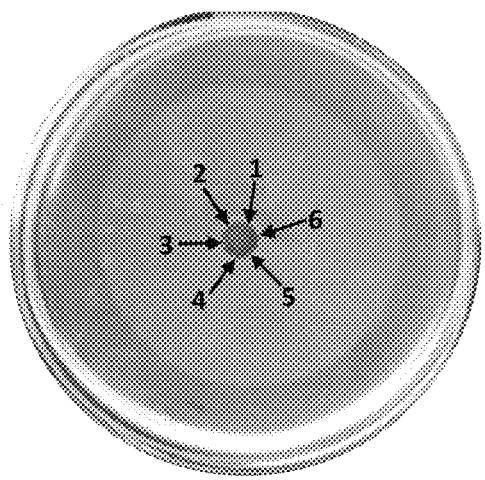
FIG. 1A-1C. Bacterial Swarming Assay. A) A random proportions mixture of non-swarming bacterial strains originally isolated from human feces from non-swarming but colony forming bacteria on agar (see methods), were used to perform the swarming assay. B) A random proportion of *Bacillus pumilus* was mixed with a mixture of strains from A) and used in the swarming assay. A swarming colony is evident and the swarm edges internal to the surfactant rim, was identified as the swarm edge. C) A random proportion of *Bacillus pumilus, Enterobacter asburiae* and mixture of strains from A) were used in the swarming assay. As in B), an intense swarm edge internal to a larger surfactant rim was identified for subsequent sampling. Six edges of the colony growing on agar or the swarm edges (as indicated by black arrows numbered 1-6) were picked and re-streaked on fresh agar plates for bacterial strain identification (see Table 1).

The invention provides a method of treating or preventing an intestinal inflammation in a subject comprising administering to the gastrointestinal tract of the subject bacterial hyperswarmers in an amount effective to treat or prevent an intestinal inflammation in a subject.

As used herein, bacterial "swarmers" refers to bacteria or strains of bacteria that aggregate and travel in the same direction. Bacterial "hyperswarmers" are identified by collective migration of bacteria over a surface that out competes its swarming counterpart and is growth independent in this activity. Hyperswarmers are out competed by counterpart swarming and non-swarming strains in biofilm formation. Hyperswarmers are intrinsically poor biofilm formers.

As used herein, "treating" or "treat" a condition means to alleviate or ameliorate or eliminate a sign or symptom of the condition that is being treated. The subject being treated can have, for example, one or more of inflammatory bowel disease, irritable bowel disease or syndrome, Crohn's disease, ulcerative colitis, gut barrier dysfunction, intestinal allergic syndrome, celiac sprue, obesity, diabetes, asthma, human immunodeficiency virus (HIV) infection, acquired immune deficiency syndrome (AIDS), and cancer, and in particular, colon cancer.

"Preventing" or "prevent" a condition means that in a subject who is free of the condition, reducing the risk of the subject developing the condition or reducing the severity of the condition that the subject develops compared to the severity of the condition that would develop in the absence of administering hyperswarming bacteria to the subject. The subject can be at risk for developing an intestinal inflammation or an illness associated with intestinal inflammation due to, for example, exposure to a toxin, a medication, poor diet, an infection such as a parasite infection or a bacterial infection, dysbiosis, bacterial overgrowth, or long-term use of an antibiotic.

Bacterial hyperswarmers can be obtained from fecal material from an animal model of inflammation or from a human with an intestinal inflammation. The bacterial hyperswarmers can be isolated from the subject, grown ex vivo, and then administered back to the same subject.

The hyperswarming bacteria are administered to the gastrointestinal tract of the subject. The bacteria, for example, can be administered orally to the subject. The bacteria can be cultured and reconstituted in common drinkables, e.g., yogurt. The hyperswarming bacteria can also be administered, for example, by rectal administration. The bacteria can be encapsulated for administration.

Also provided is a method of isolating a bacterial strain for treating an intestinal inflammation from a complex bacterial mix, the method comprising isolating bacterial hyperswarmers as a single bacterial strain from fecal material on a plate agar assay under aerobic conditions; and propagating the bacterial hyperswarmers in culture in order to isolate a bacterial strain for treating an intestinal inflammation from a complex bacterial mix.

Bacterial hyperswarmer bursts can be identified as emanating from an edge of a bacterial swarming colony. Bacteria can be taken from a sample around the edge of a bacterial swarming growth and then recultured. Culture plates can be incubated, for example, overnight at 35° C.

Also provided is a method of diagnosing an intestinal inflammation in a subject, the method comprising culturing bacteria from a fecal sample from the subject under aerobic conditions, and examining the culture for the presence of bacterial hyperswarmers, wherein bacterial hyperswarmer are identified as one or more bursts emanating from the edge of a bacterial swarming colony, and wherein the presence of bacterial hyperswarmers in a fecal sample from a subject is indicative that the subject has an intestinal inflammation.

Also provided is a composition for treating an intestinal inflammation in a subject, the composition comprising bacterial hyperswarmers in an amount effective to treat an intestinal inflammation. The composition can be formulated for oral administration or for rectal administration. The composition can be encapsulated.

Bacterial hyperswarmers, include, but are not limited to, *Escherichia coli; Klebsiella pneumoniae, Citrobacter koseri, Serratia marcescens, Proteus mirabilis, Acinetobacter* sp., *Bacillus* sp., *Enterobacter* sp., *Enterobacter asburiae, Enterobacter cloacae* and *Cedecea davisae*.

The subject can be any animal, such as a farm animal or livestock, and is preferably a human. The animal can be one that is raised or used in an agricultural setting to produce food, fiber and/or labor. The animal can be an animal that is under veterinary care.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Introduction and Overview

The present results show that bacterial hyperswarming is highly predictive of the presence or evolution of pathophysiology in mice and humans. Bacterial hyperswarmers can be isolated as a single strain from feces on a plate agar assay. These strains can be propagated in culture to maintain hyperswarming properties on agar. As opposed to bacterial biofilms[11], hyperswarmers protect against inflammation in mice. The results demonstrate a completely new consequence of bacterial hyperswarming in mice and humans. Specifically, a general state of actively impaired health selects for the presence of intestinal bacterial hyperswarmers that can be isolated to purity. Hyperswarming strains isolated from both mice and humans protect against intestinal inflammation in mice. The assay disclosed herein can be used as a diagnostic test for the discovery of impaired health (e.g., less than 5% of the global population has no burden of disease)[12], thus providing a basis for disease specific screens.

Materials and Methods

Swarming Assay.

These methods are significantly modified from published assays[15].

Identification of Bacterial Strains.

Subcultured bacteria from samples taken around the edge of swarming growth were re-subcultured to MaConkey II, Columbia Nalidixic Acid (CNA) with 5% sheep blood, and Trypticase Soy Agar with 5% sheep blood plates (Becton Dickinson, Sparks, Md.). Culture plates were incubated overnight at 35° C. A minimum of three colonies from each sample were identified by MALDI-TOF analysis using a MALDI Biotyper (Bruker Daltonics, Billerica, Mass.) in conjunction with Real Time Classification software (Bruker Daltonics, version 3.1). When evident, colonies with varied lactose fermentation reactions and/or colony morphologies were chosen for MALDI identification. Colonies were identified by directly transferring the bacteria to a MALDI target plate followed by the addition of 70% formic acid (Sigma-Aldrich, St. Louis, Mo.) and HCCA (α-cyano-4-hydroxycinnamic acid) matrix (Bruker Daltonics). When necessary, colonies with low MALDI identification scores (0-1.999) were subcultured, and a tube-based extraction was performed to attempt to improve the identification score. Briefly, colonies were added to 300 µl of water and emulsified followed by the addition of 100% ethanol (Sigma-Aldrich). The bacterial suspension was centrifuged (13,000 rpm, 2 min, RT) and the supernatant removed from the bacterial pellet. To extract the bacterial proteins, 50 µl of 70% formic acid and 50 µl of acetonitrile (Sigma-Aldrich) were added to the bacterial pellet, the sample was vigorously vortexed, and again centrifuged. The supernatant (1 µl) was spotted onto MALDI targets in triplicate for identification. MALDI identification scores of 1.7-1.999 were considered indicative of a reliable genus level identification whereas a MALDI score ≥2.0 indicated reliable genus and species unless otherwise indicated.

DSS colitis Model in Mice.

The model for dextran sulfate sodium (DSS)-induced colitis in mice has been published by several groups[18]. Briefly, 6-8 week old C57BL/6 mice were administered daily DSS (3% w/v) (MW 36-50 kDa) from day 0-6, and mice were sacrificed and the entire small and large bowel prepped for histological analysis in paraffin using the swiss roll technique. Histologic scoring of the extent of colonic inflammation was performed as previously published[19]. Individual strains (in 100 µl of media, LB or PBS) (grown to OD1.0) used for oral gavage experiments in mice (starting day 0 in the morning, with DSS administered in the evening with the regular water change) were used for experiments involving effects on intestinal inflammation. For heat-killed bacteria, 1 ml of each strain (grown to OD1.0) was placed in a heat box at 99 C for 15 min. The bacteria were centrifuged at 10,000×g for 1 min, and supernatant discarded. The pellet was re-suspended in 1 ml LB or PBS buffer (pH 7.4) and aliquoted in 100 µl stocks for use per mouse.

Results and Discussion

Figure 1B:
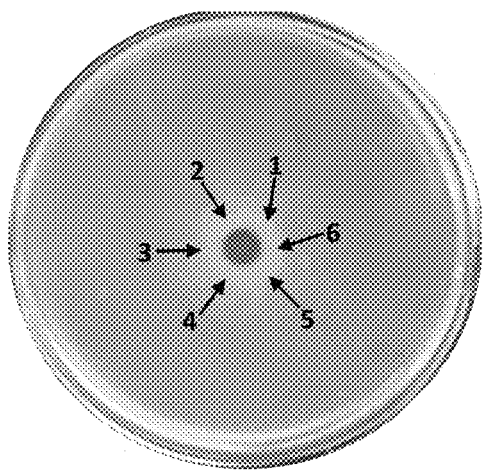
Figure 1C:
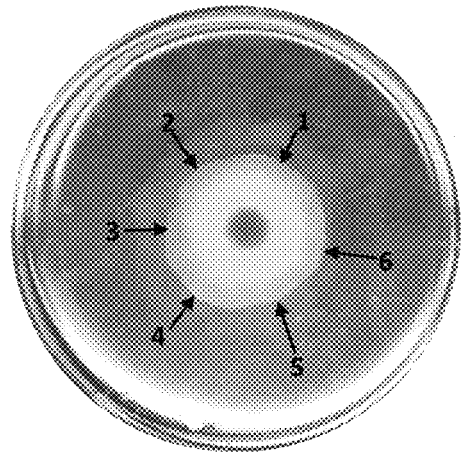
Figure 2:
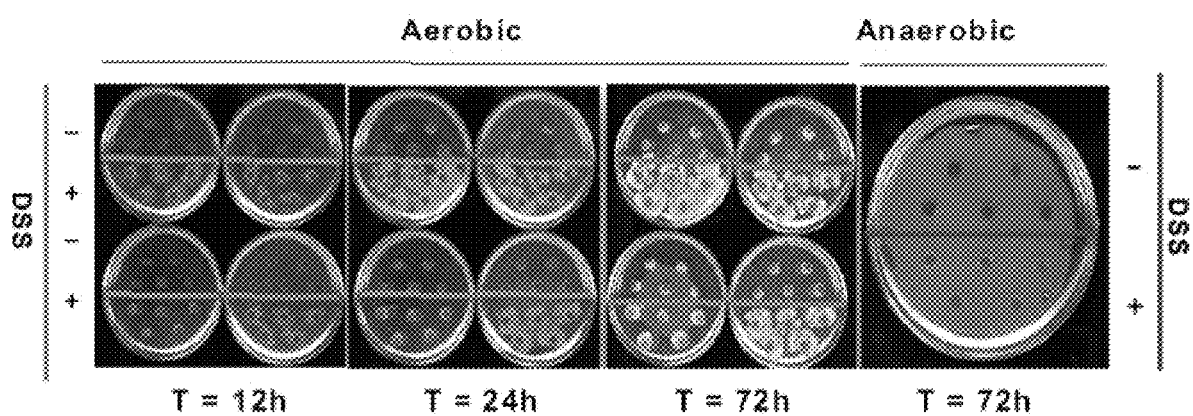
FIG. 2. Fecal Bacterial Swarming Assay. Four to six week old female inbred C57BL/6 mice (n=3/group) were subject to the DSS treatment protocol (see methods). At necropsy, feces was collected, pooled for each treatment group (+, −DSS) and swarming assay (see methods) performed over time (T) 0-72 h. The swarming assays were conducted under anaerobic and aerobic conditions (see methods). +, mice exposed to DSS; −, mice exposed to DSS vehicle. The aerobic and anaerobic bars segregate the "+" and "−" feces from DSS exposed mice. Note, for each pooled feces, 30 swarm spots were plated on agar. The DSS experiment was repeated at least two times (as shown). There was no activity in the agar plates incubated under anaerobic conditions and only the final data at 72 h is shown.
Figure 3:
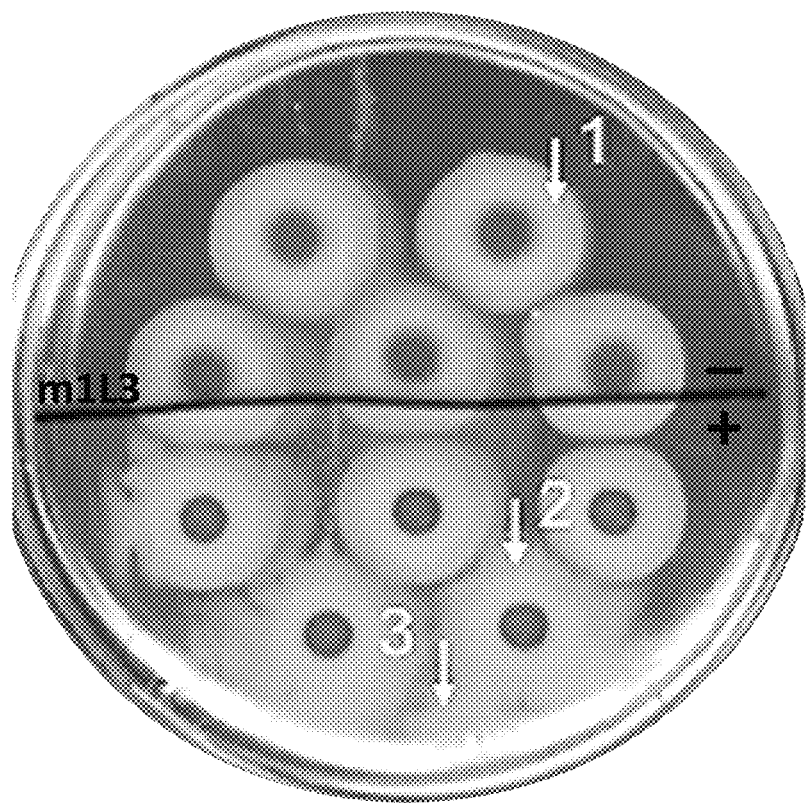
FIG. 3. Swarming assay performed in feces isolated from experiments conducted in FIG. 2. The plates were observed for 48 h and arrows indicate specific edges that were sampled for identification of bacteria. The numbers indicate isolation of strain 1 (SM1), strain 2 (SM2), and strain 3 (SM3) from 1, 2 and 3, respectively.

To test whether bacterial hyperswarming is a property that can be reflective of human and rodent health, a modified swarming assay was developed based on an established agar based plate assay utilized for single strain swarmers[15]. Based on arguing the principle of selfish dominance in the Nash equilibrium example of Prisoner's Dilemma as it is applied to fate decisions in adverse times[16,17], in this assay, a mixed bacterial culture generally gives rise to a single bacterial strain populating the leading edge of the swarm colony on agar (FIG. 1A-C; Table 1). Next, it was tested whether singular bacterial hyperswarmers could be detected and/or isolated from mammalian feces as the latter serves as an excellent model for the study of a heterogenous microbial culture. Mice were exposed to an intestinal epithelial inflammatory toxin, dextran sodium sulfate (DSS), or vehicle (FIG. 2). Pooled feces exposed to the swarming assay yielded single strains that varied depending on the type of intestinal inflammation observed (Table 2). Hyperswarming was uniformly absent in vehicle exposed mice feces. However, in a single experiment, a single identical isolate was found from two different fecal samples from mice exposed in vivo to vehicle or DSS (FIG. 3). Additionally, hyperswarmer bursts were observed emanating from swarming colonies of DSS exposed mice. Individual strains were isolated from the leading edge of these swarm colonies and were gram stain negative rods with flagella.

Figures 4A, 4B:
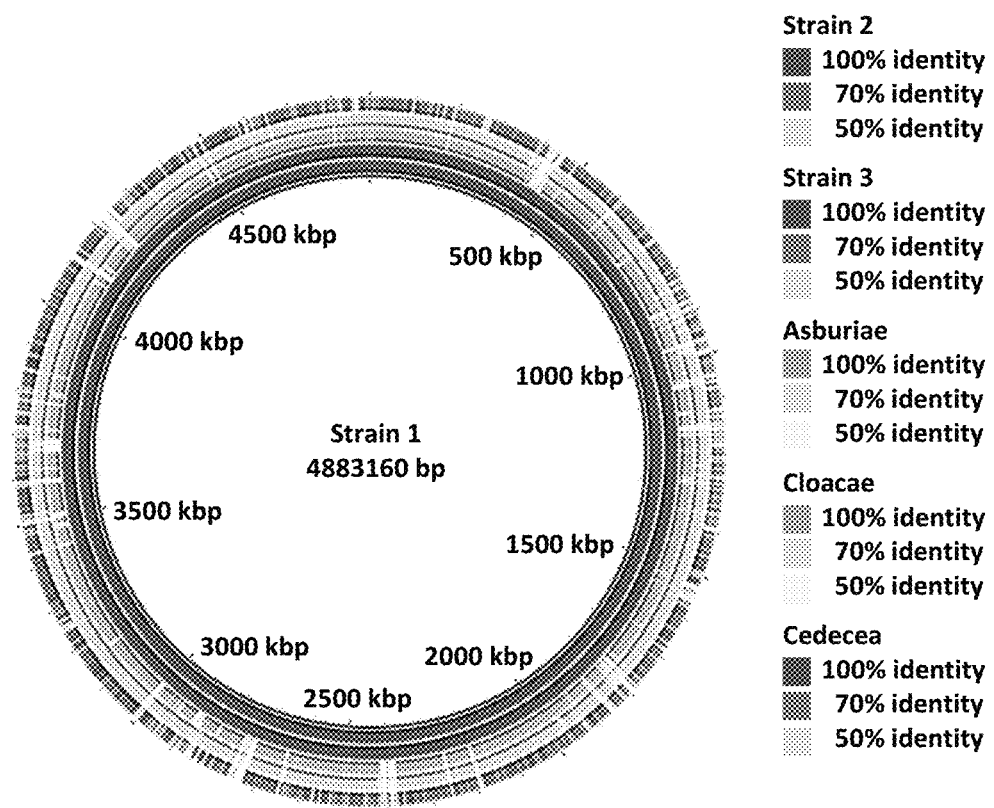
FIG. 4A-4B. Genomic analysis of three Entereobacter strains. A) Genome coverage, length, and total number of genes per Entereobacter strains 1, 2 and 3. B) Comparison of the genomes of the *Enterobacter* strains with related strains, *Enterobacter asburiae, Enterobacter cloacae*, and *Cedecea davisae*. The innermost ring represents BLAST hits to strain 2, moving outward the rings represent BLAST hits to strain 3, *E. asburiae, E. cloacae,* and *C. davisae*. Figure plotted with BLAST Ring Generator (BRIG) (world wide web brig.sourceforge.net/PMID: 21824423).

Sequencing and assembly was done at the Yale Center for Genome Analysis. PacBio® Single Molecule Real Time (SMRT) sequencing was used to generate long single pass reads for each of the three strains. The Hierarchical Genome Assembly Process (HGAP), developed specifically for SMRT sequencing, was used for assembly of the genomes. SMRT Sequencing and HGAP assembly yielded one contig for each strain, with each strain having >100 average coverage depth. Each genome was annotated using the RAST (Rapid Annotation using Subsystem Technology) pipeline (PMID 18261238), which includes gene calling and functional annotation. Overall statistics for the genomes are shown in FIG. 4A.

A whole genome analysis of the genomes of three *Enterobacter* strains and three related strains, *Enterobacter asburiae*, *Enterobacter cloacae*, and *Cedecea davisae*, revealed that while the three strains isolated here were extremely similar to each other (pairwise alignments of the strains were >99% similar over >80% of the genome), these genomes are distinct from other available related strains genomically. This genomic distance is demonstrated graphically by gaps, indicating missing regions that are part of the genomes of the three strains from the related strains (FIG. 4B).

Bacterial swarming was also observed in additional models of intestinal inflammation and/or dysbiosis like pregnane x receptor knockout mice; indomethacin treated mice with enteritis; and 2,4,6-Trinitrobenzenesulfonic acid (TNBS)-exposed mice with colitis [data not shown].

To determine the human relevance of bacterial swarming, feces and/or colonoscopy washings were obtained from individuals with an active illness (irritable bowel disease (IBD), Crohn's disease, ulcerative colitis; diabetes, asthma, HIV) as well as age and gender matched controls (those without a clinically active illness) (Table 3). Within the sampling pool, bacterial hyperswarming was only present in cases with overt or clinically active disease (IBD, cancer, asthma, diabetes, obesity with or without co-existing hypertension). In all these diseases, there is a growing association between abnormal intestinal microbial homeostasis and disease pathology. While hyperswarmers could be absent in such cases, not even a single fecal sample harboring hyperswarmers could be identified in the "control" population (Table 4A). In the test population, the disease prevalence was 63.4% and specificity and positive predictive value of the test for disease as defined was 93.3 and 94.1%, respectively. On the other hand, the sensitivity and negative predictive value of the test was only 61.5 and 58.3%, respectively (Table 4B). Together, in humans, these data indicate that hyperswarming can serve as a biomarker of an unhealthy individual.

Figure 5A:
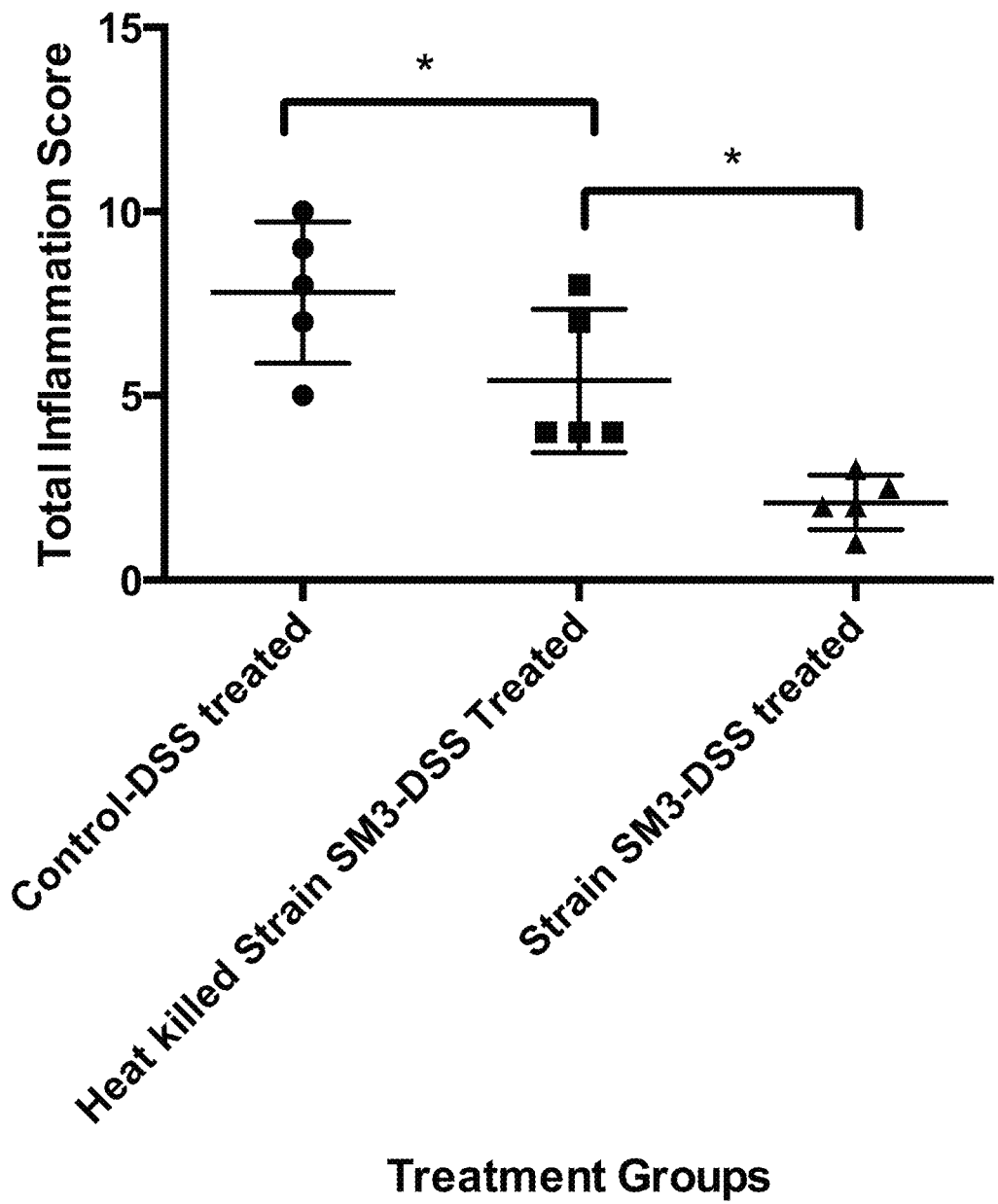
FIG. 5A-5C. Oral Gavage of hyperswarming strains isolated from mice and humans to colitic mice. Bacterial hyperswarming strains protect against intestinal inflammation compared to their heat-killed controls. A) Hyperswarming strain SM3 from mice. B) Non-swarming strain SM1 from mice. C) Hyperswarming *S. marcescens* isolated from a human patient with ulcerative colitis.
Figure 5B:
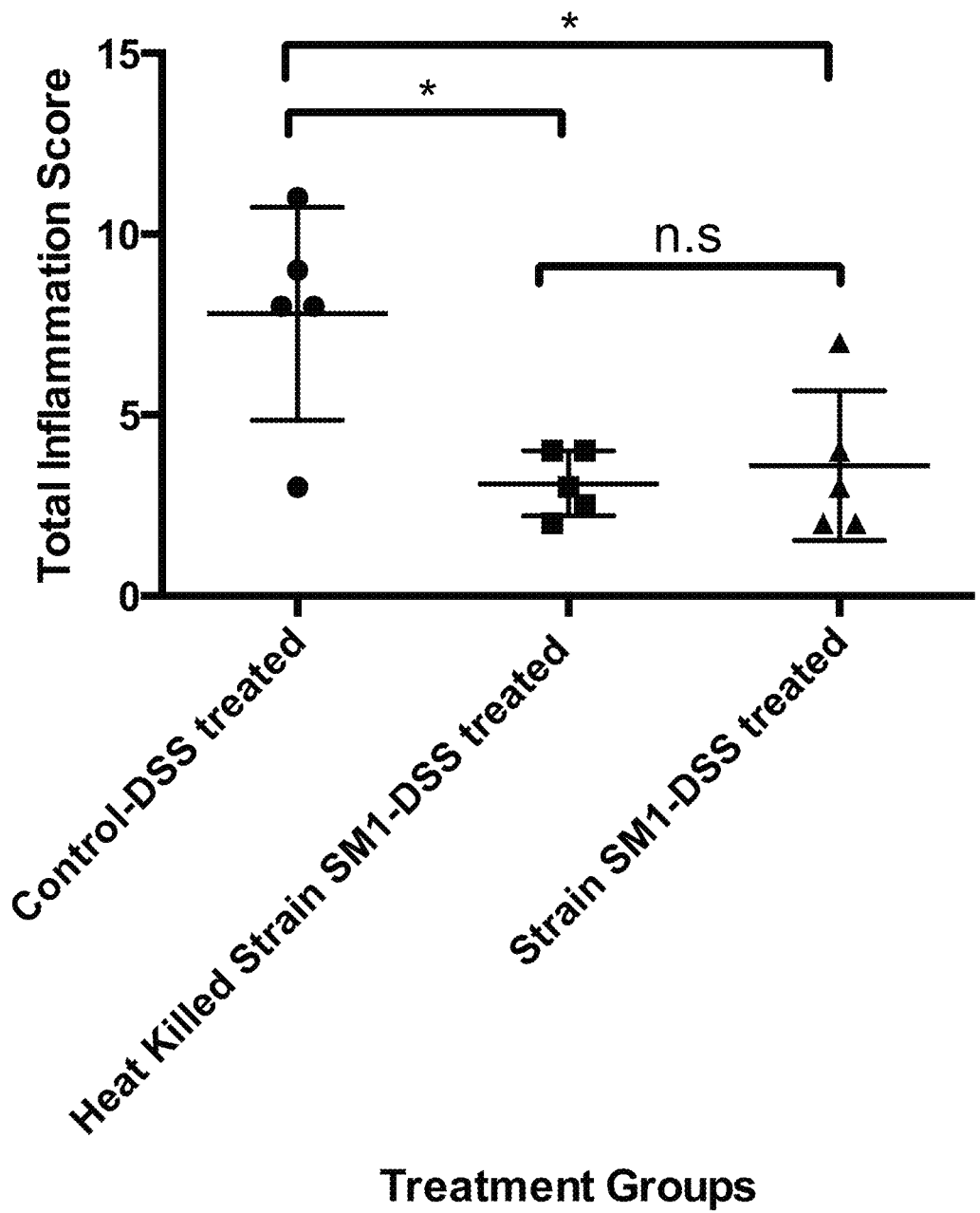
Figure 5C:
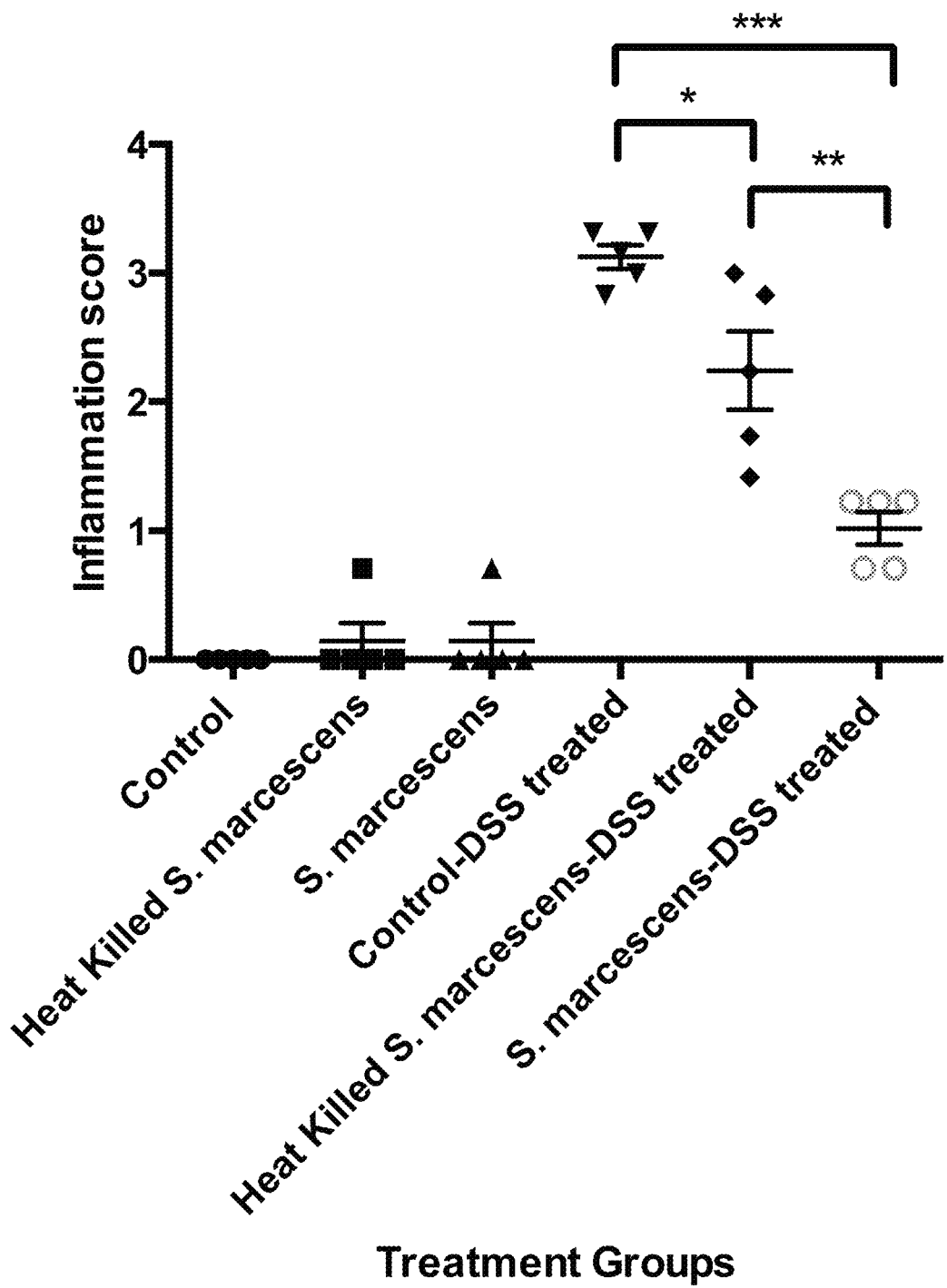
Figure 6:
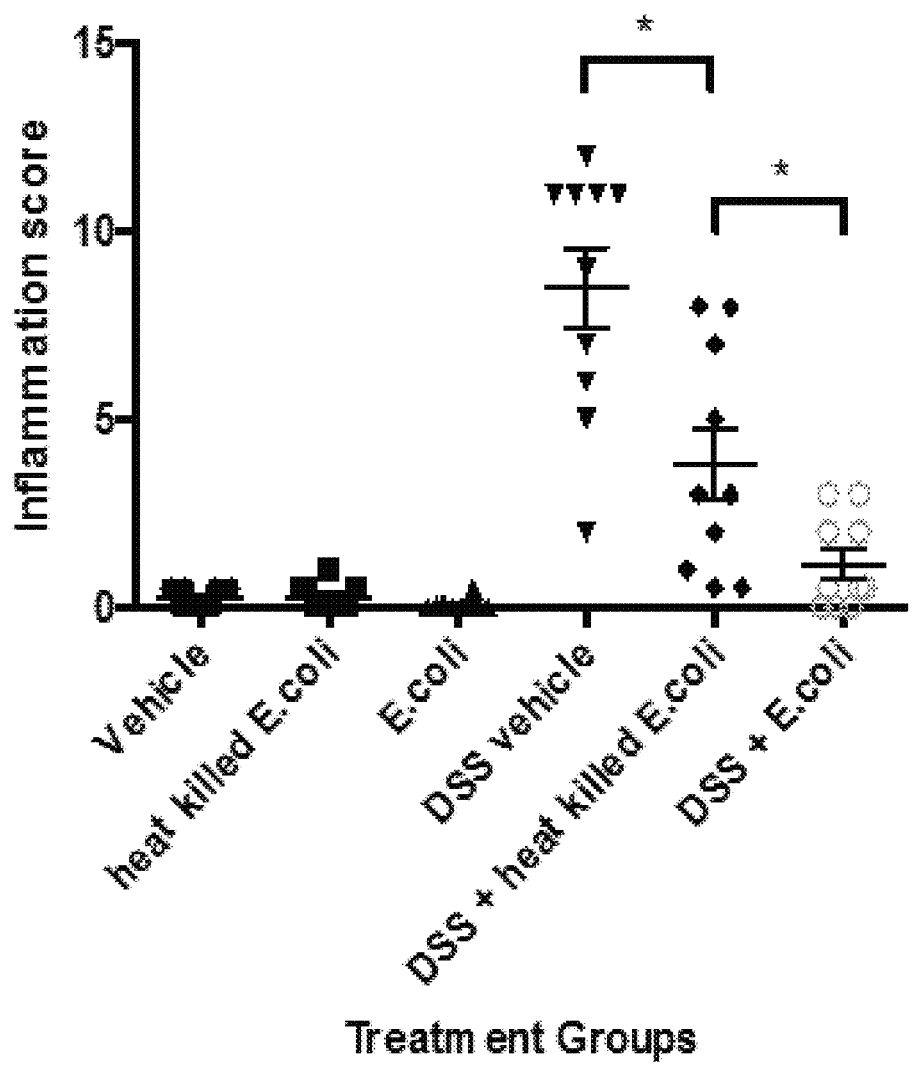
FIG. 6. Effect of gavaged *E. coli* (delayed hyperswarmer isolated from a patient with inflammatory bowel disease) on intestinal inflammation in mice (n=10 mice/grp). The results show that hyperswarming *E. coli* have a significant protective effect on DSS-mediated intestinal inflammation (*$p<0.05$, One-way ANOVA). Non-swarming *E. coli* do not protect (data not shown).
Figure 7:
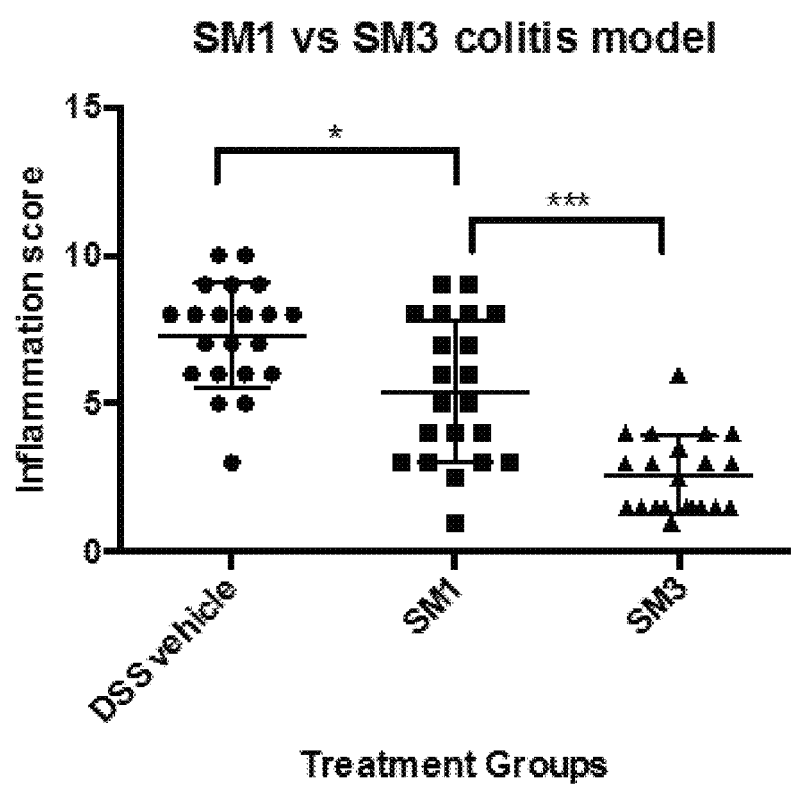
FIG. 7. Effect of SM3 (hyperswarmer) versus SM1 (non-swarmer) strains on intestinal inflammation in mice. Data reveal a significant effect of SM3 versus SM1 on suppression of intestinal inflammation (n=21 mice/grp) (*, *** $p<0.05$, One-way ANOVA).
Figure 8:
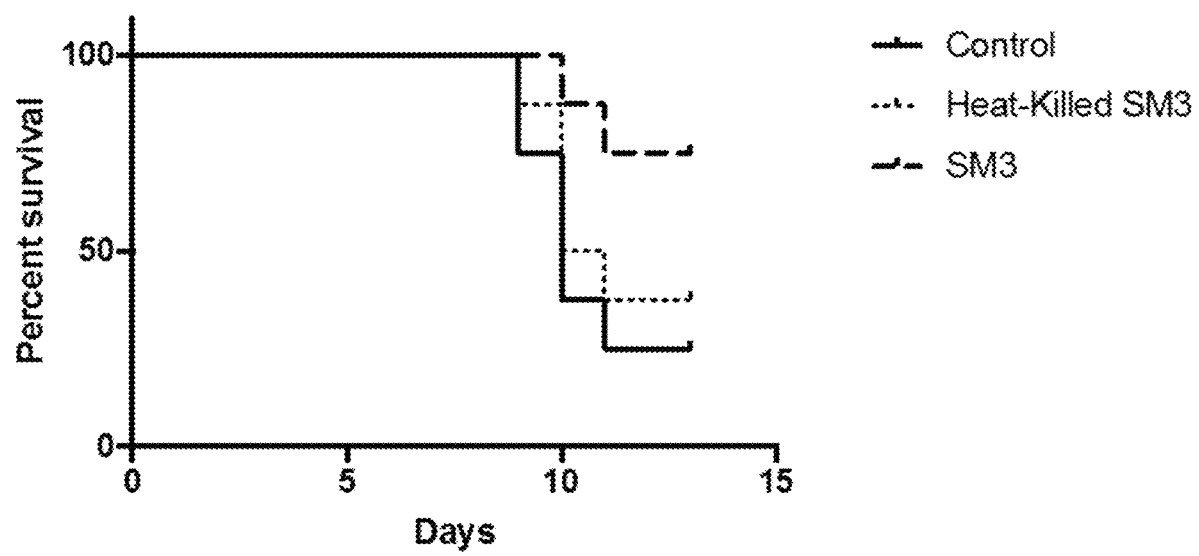
FIG. 8. Oral Gavage of heat-killed SM3 and wild-type live SM3 strains to SCID.NOD mice (lacking adaptive immune system but with functional components of innate immunity) (n=8/grp) showing that live SM3 (but not heat-killed SM3) significantly protects from DSS-induced colitis ($p<0.03$). These data suggest that the protection against inflammation by hyperswarming strains like SM3, likely depend on altering innate immunity rather than adaptive immunity.
Figure 9A:
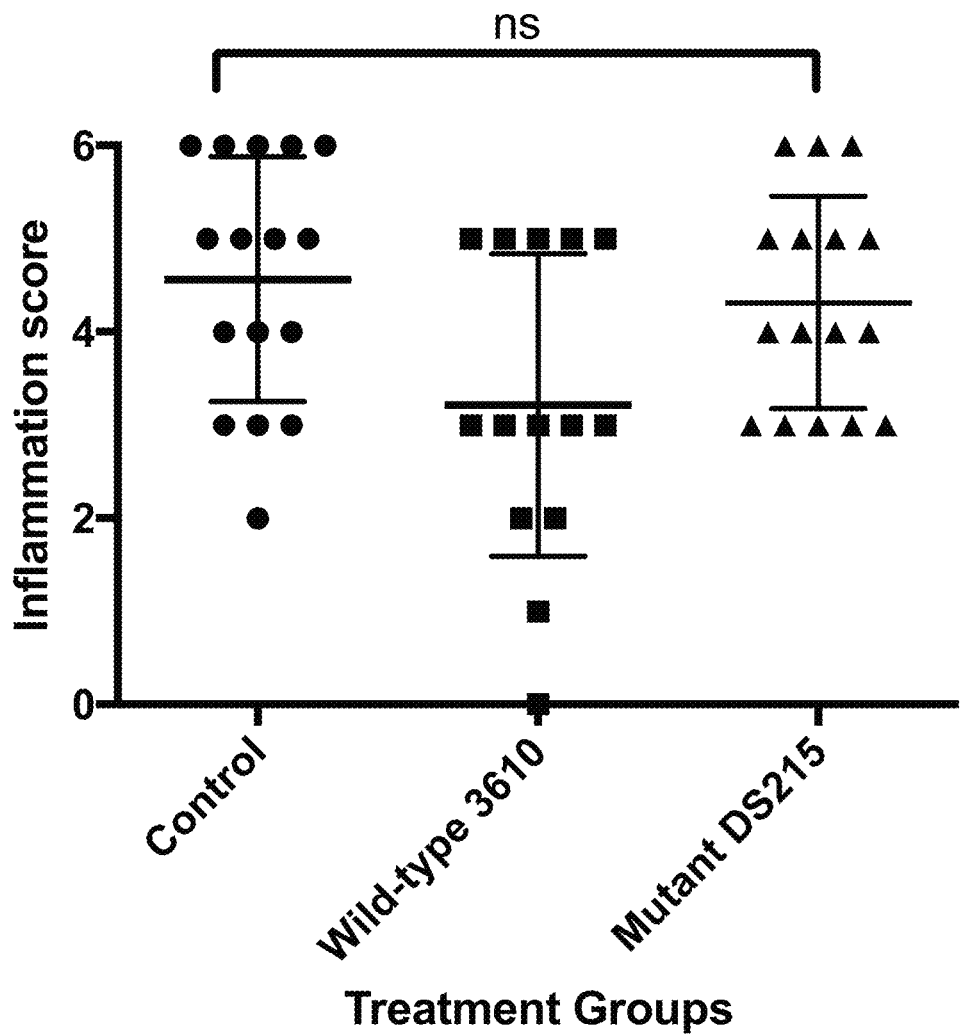
FIG. 9A-9B. A) Oral Gavage of *B. subtilis* wild-type (3610) and SwrA mutant (DS215) strains to mice with DSS-induced colitis. The wild-type but not the mutant DS215 strain protects against intestinal inflammation. The wild-type strain (3610) possesses intact and functional flagella and is swarming competent[20]. By contrast, the DS215 mutant strain has a motor component deficiency, and although it possess intact flagella, is swarming deficient[21]. Since the scores have large variability, and the DS215 group has equivalent mean/variance to controls, the mutant and control groups were collapsed, and compared to the wild-type (3610) in (B). B) The 3610 strain shows significant protection against intestinal inflammation.
Figure 9B:
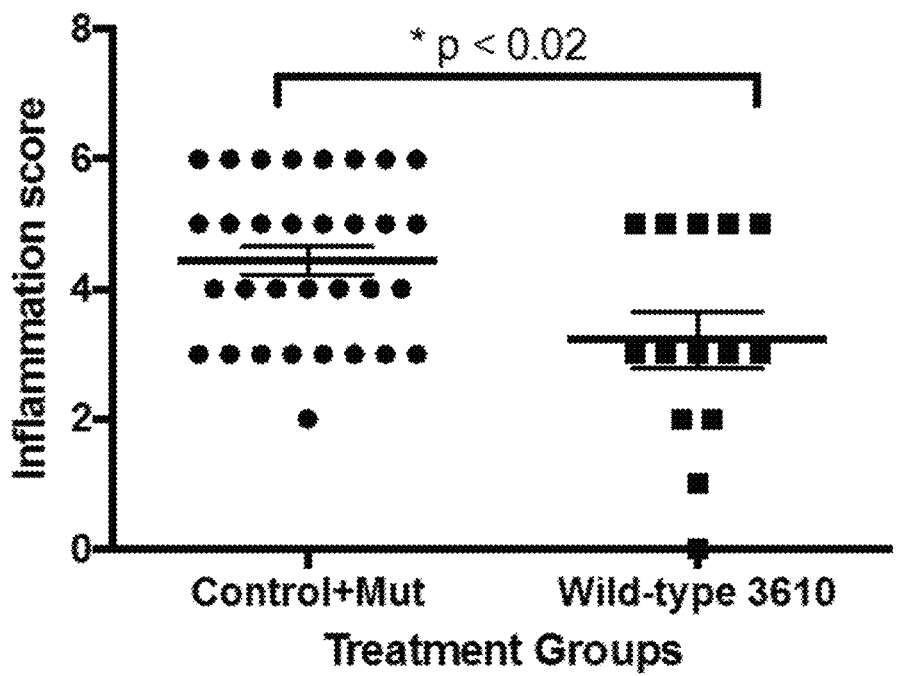
Figure 10:
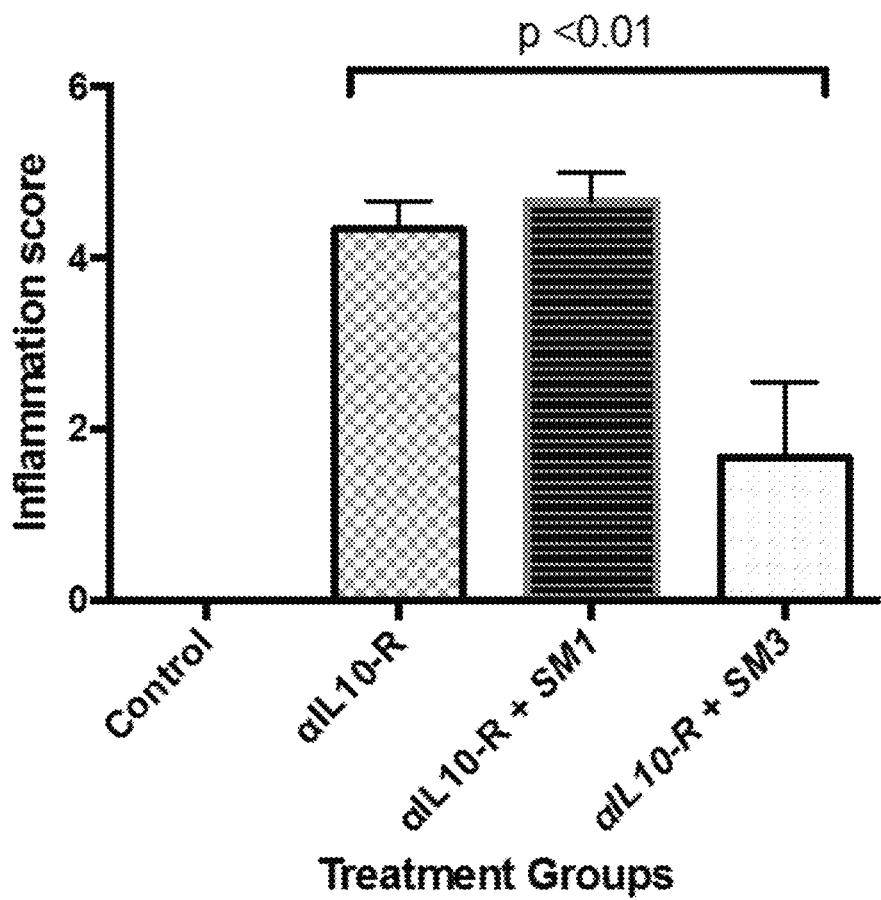
FIG. 10. Oral Gavage of two swarming strains, one SM1 (moderate swarmer) and the second, SM3 (hyperswarmer), to TLR5 deficient mice with colitis secondary to administration of the IL10 antibody[22]. SM3 strain (but not SM1) protects against inflammation in this model of colitis. This suggests that protection by SM3 is likely to be independent of TLR5, which is a major receptor of flagellin.
Figure 11A:
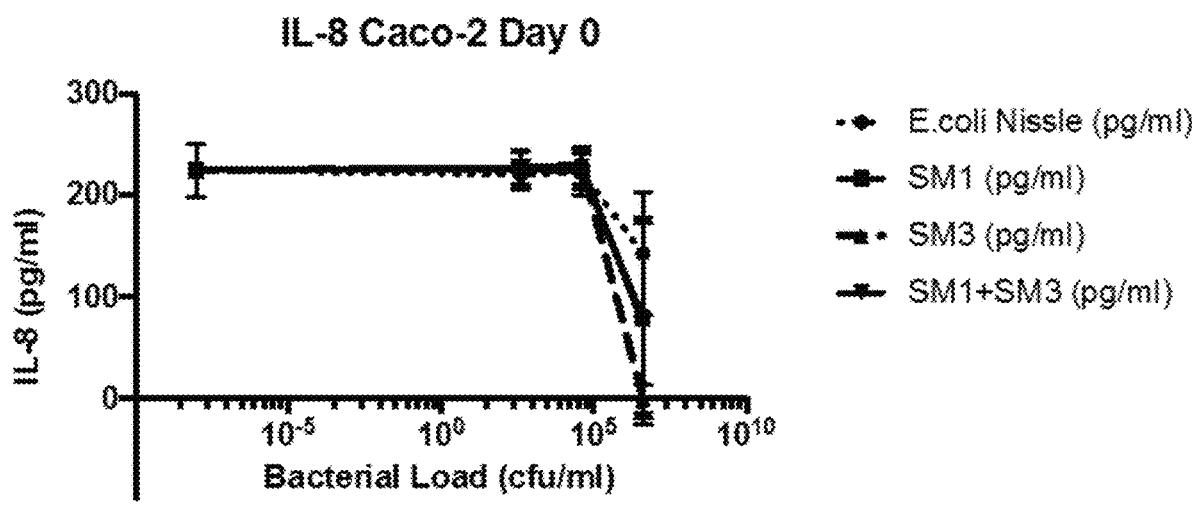
FIG. 11A-11B. A) IL-8 Casco-2 Day 0, and B) IL-6 Casco-2 Day 0. Caco-2 cells (ATCC) were plated day 0 and treated with inflammatory factors (IL-1beta 25 ng/ml, LPS 10 µg/ml, TNF-alpha 50 ng/ml and IFN-gamma 50 ng/ml[23] and cells overlaid with SM1 or SM3 or the combination (1:1) of SM1 and SM3. ELISA assays were performed for Caco-2, 0-day samples. Interestingly, bacteria strands behaved similarly to *E. coli* Nissle showing slightly higher suppression of the expression of the cytokines but bioequivalent. It is interesting that for both assays, the results of bacteria regarding *E. coli* Nissle was similar and only SM3 showed a stronger repression of IL-8 expression.
Figure 11B:
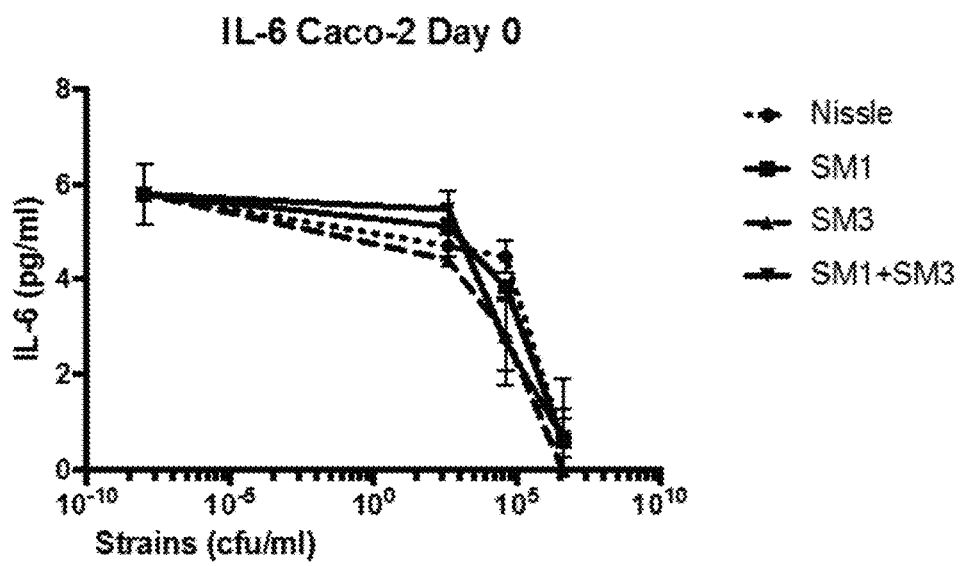

Next, to assess whether bacterial hyperswarming is simply a marker of an unhealthy microbiome or has a phenotypic role in modifying host health, mice were exposed to oral gavage (~$10^8$ cfu in 100 microL media) of a swarming strain (strain 3) originally isolated from colitic mice. This strain (SM3) was administered on the day dextran sodium sulfate (DSS) was administered to mice. On day 6, post gavage, mice were sacrificed and intestines evaluated for degree of inflammation using a well-published scoring system[18]. The heat-killed SM3 did protect against inflammation but there was an even more significant effect of live SM3 on inflammation (*p<0.001, One-way ANOVA) (FIG. 5A). These results are consistent with swarming strains protecting against intestinal inflammation. As a corollary, strain 1 (SM1), which is a non-swarmer, did not protect against inflammation when compared with its heat-killed counterpart, indicating that the "swarming" phenotype is linked to protection against intestinal inflammation in this model (FIG. 5B). Indeed a direct comparison of live Strains, SM1 and SM3, reveal that SM3 is more significant in abrogating intestinal inflammation when compared with SM1. Furthermore, *S. marcescens*, originally isolated from a patient with ulcerative colitis, displays hyperswarming properties and when mice were administered this strain, there was significant protection against intestinal inflammation (*, , *p<0.001, One-way ANOVA) (FIG. 5C). Similarly, swarming *E. coli* isolated from another patient with colitis yielded similar results. In contrast, there was no difference in the protection of intestinal inflammation with live *E. coli* isolated from patients with quiescent colitis versus its heat-killed counterpart. Live swarming strains could protect against systemic inflammation via an intestinal innate immune mechanisms. This implies that swarming strains can be detected, isolated and purified for ultimate therapeutic applications in a variety of systemic conditions.

The present invention provides a cost-efficient method to obtain single species bacterial hyperswarming isolates from animals with chemically-induced colitis based on soft agar swarming. This method allows for detection of hyperswarming bacteria with 2-24 h from plating. Leading edge sampling and re-plating of sample is followed by growth in standard Luria Broth and can be performed within 36-48 h. Oral gavage of large quantities of the swarming species (regardless of the species) causes no appreciable pathology in mice. However, when administered with the chemical induction of intestinal inflammation, hyperswarming bacteria significantly protect the mice from inflammation. Human bacterial hyperswarmers, isolated from patients with inflammatory bowel disease (IBD) have also been isolated and administered to mice with colitis—uniformly, regardless of the specific species, hyperswarming bacteria protect against intestinal inflammation.

The invention provides a efficient herd-specific approach to combat acute and chronic gastrointestinal diseases in farm animals. The approach entails efficient isolation of swarming bacterial species (swarmers) from a single acutely ill animal to prevent disease in the herd of animals through oral gavage of purified hyperswarmers. Swarming bacteria can be isolated using an unbiased soft agar assay with whole fecal samples. The yield within 24 hours is a single bacterial species that may be isolated and amplified for probiotic use.

The present results demonstrate several key new points, including:
  establishment of a new method for identification of hyperswarmers from a mixed population of bacteria;
  isolation of single bacterial strains from the swarming assay;
  demonstration that the presence of hyperswarming in this assay has a high specificity and positive predictive value in detecting disease, as defined by "systemic inflammatory syndromes" in the test population, including but not limited to inflammatory bowel syndromes;
  identification of a new strain of *enterobacter* family that affords protection against intestinal inflammation; and
  demonstration of a method to isolate bacterial strains with the hyperswarming property that protect against intestinal inflammation, providing for development of individualized probiotics for the prevention and/or treatment of intestinal inflammation.

The advantages of the present method include:

easy procedure to prepare and obtain hyperswarming isolates at a very low cost;

the bacterial species is not important, rather the bacterial property is, so technically any species with this property can be used, which expands the number of species that could serve in a probiotic role;

individualizes treatment to either the animal that is sick with a particular gastrointestinal pathology and/or the herd or contained animal colony;

hyperswarmers can be stored and reused with time.

TABLE 1

Identification of bacterial colonies isolated from growth edge.

| Sample Number | MALDI Identification | MALDI Identification Score (Mean) [A] |
|---|---|---|
| 1-1 | Klebsiella pneumoniae | 2.26 |
|  | Escherichia coli | 2.06 |
| 1-2 | Klebsiella pneumoniae | 2.24 |
|  | Escherichia coli | 2.33 |
| 1-3 | Klebsiella pneumoniae | 2.20 |
|  | Escherichia coli | 2.33 |
|  | Acinetobacter sp. | 1.82 |
| 1-4 | Klebsiella pneumoniae | 2.12 |
|  | Acinetobacter sp. | 1.76 |
| 1-5 | Klebsiella pneumoniae | 2.12 |
| 1-6 | Klebsiella pneumoniae | 2.24 |
|  | Escherichia coli | 2.14 |
| 2-1 | Bacillus sp. | 1.81 |
| 2-2 | Bacillus sp. | 1.83 |
| 2-3 | Bacillus sp. | 1.79 |
| 2-4 | Bacillus sp. | 1.80 |
| 2-5 | Bacillus sp. | 1.80 |
| 2-6 | Bacillus sp. | 1.84 |
| 3-1 | Enterobacter asburiae [B] | 2.24 |
| 3-2 | Enterobacter asburiae | 2.28 |
| 3-3 | Enterobacter asburiae | 2.31 |
| 3-4 | Enterobacter asburiae | 2.25 |
| 3-5 | Enterobacter asburiae | 2.27 |
| 3-6 | Enterobacter asburiae | 2.21 |

[A] MALDI identification scores ≥2.0 indicate reliable species level identification. Identification scores between 1.7-1.99 indicate a reliable identification to the genus level only.
[B] Enterobacter asburiae is a member of Enterobacter cloacae complex. The species level identification of E. cloacae complex members by MALDI must be confirmed by other methods.

TABLE 2

Isolation of Bacterial Strains on the Swarming Assay from Feces [#].

| Sample | Swarming | Strain Isolated |
|---|---|---|
| Human IBD | + | Escherichia coli |
| Human IBD | + | Escherichia coli |
| Human anal fistula | + | Escherichia coli |
| Human IBD | +[1] | Klebsiella pneumoniae |
| Healthy Human | −[2] | Klebsiella pneumoniae |
| Human IBD | + | Citrobacter koseri |
| Human IBD | −[3] | Morganella morganii |
| Human adenomatous polyp | + | Serratia marcescens |
| Mouse | + | Proteus mirabilis |
| Mouse | + | Proteus mirabilis |
| Mouse DSS colitis | + | Single enterobacter species (see FIG. 1) |
| Mouse TNBS colitis | + | Single enterobacter species (see FIG. 1) |

[#] Human or mouse feces was subject to the swarming assay and any swarm colony detected within 24 h was swabbed for strain identification. In addition, delayed swarmers were classified as negative but their swarm edge also yielded single strain isolates:
[1] Feces from patient with clinically controlled Crohn's disease with moderate surfactant edge detected at 74 h.
[2] Classified as non-swarmer; however, a very minimal surfactant edge present at 24 h and no progression thereafter.
[3] Feces from patient with clinically controlled Crohn's disease with surfactant edge detected at 48 h.

TABLE 3

Patient characteristics.

| | | Disease | |
|---|---|---|---|
| | | + | − |
| Age | Mean (±SD) | 50.1 (±16.8) | 54.6 (±10.2) |
|  | Median [10] | 51.5 (21-70) | 52 (35-71) |
| Gender | Females | 16 | 8 |
|  | Males | 10 | 7 |

TABLE 4

Diagnostic test potential of swarming assay as a function of an unhealthy microbiome.

A.

| | Disease*+ | Disease− |
|---|---|---|
| Swarm+ | 16 | 1 |
| Swarm− | 10 | 14 |

B.

| Statistic | Value | 95% CI |
|---|---|---|
| Sensitivity | 61.54% | 40.57% to 79.77% |
| Specificity | 93.33% | 68.05% to 99.83% |
| Positive Likelihood Ratio | 9.23 | 1.36 to 62.82 |
| Negative Likelihood Ratio | 0.41 | 0.25 to 0.68 |
| Disease Prevalence | 63.41% | 46.94% to 77.88% |
| Positive Predictive Value | 94.12% | 71.31% to 99.85% |
| Negative Predictive Value | 58.33% | 36.64% to 77.89% |

*Defined as individuals with clinically established active inflammatory bowel disease (Crohn's disease or ulcerative colitis), obesity (BMI > 35), diabetes, asthma, and HIV.

REFERENCES

1 Verstraeten, N. et al. Living on a surface: swarming and biofilm formation. *Trends Microbiol* 16, 496-506, doi: 10.1016/j.tim.2008.07.004 (2008).

2 Kearns, D. B. A field guide to bacterial swarming motility. *Nat Rev Microbiol* 8, 634-644, doi:10.1038/nrmicro2405 (2010).

3 Gonzalez-Sarrias, A., Larrosa, M., Tomas-Barberan, F. A., Dolara, P. & Espin, J. C. NF-kappaB-dependent anti-inflammatory activity of urolithins, gut microbiota ellagic acid-derived metabolites, in human colonic fibroblasts. *The British journal of nutrition* 104, 503-512, doi:10.1017/s0007114510000826 (2010).

4 Dejea, C. M. et al. Microbiota organization is a distinct feature of proximal colorectal cancers. *Proceedings of the National Academy of Sciences of the United States of America* 111, 18321-18326, doi:10.1073/pnas.1406199111 (2014).

5 Johnson, C. H. et al. Metabolism Links Bacterial Biofilms and Colon Carcinogenesis. *Cell Metab, doi:* 10.1016/j.cmet.2015.04.011 (2015).

6 Villanueva, M. T. Metabolism: Bacterial biofilms may feed colon cancer. *Nat Rev Cancer* 15, 320, doi: 10.1038/nrc3970 (2015).

7 Breidenstein, E. B., de la Fuente-Nunez, C. & Hancock, R. E. *Pseudomonas aeruginosa*: all roads lead to resistance. *Trends Microbiol* 19, 419-426, doi:10.1016/j.tim.2011.04.005 (2011).

8 Butler, M. T., Wang, Q. & Harshey, R. M. Cell density and mobility protect swarming bacteria against antibiotics. *Proceedings of the National Academy of Sciences* of the United States of America 107, 3776-3781, doi:10.1073/pnas.0910934107 (2010).
9 Rozalski, A., Sidorczyk, Z. & Kotelko, K. Potential virulence factors of Proteus bacilli. Microbiol Mol Biol Rev 61, 65-89 (1997).
10 Ranger, G. S. Current concepts in colorectal cancer prevention with cyclooxygenase inhibitors. Anticancer Res 34, 6277-6282 (2014).
11 von Rosenvinge, E. C., O'May, G. A., Macfarlane, S., Macfarlane, G. T. & Shirtliff, M. E. Microbial biofilms and gastrointestinal diseases. Pathog Dis 67, 25-38, doi:10.1111/2049-632x.12020 (2013).
12 Global, regional, and national incidence, prevalence, and years lived with disability for 301 acute and chronic diseases and injuries in 188 countries, 1990-2013: a systematic analysis for the Global Burden of Disease Study 2013. Lancet, doi:10.1016/s0140-6736(15)60692-4 (2015).
13 Barak, J. D., Gorski, L., Liang, A. S. & Narm, K. E. Previously uncharacterized Salmonella enterica genes required for swarming play a role in seedling colonization. Microbiology (Reading, England) 155, 3701-3709, doi:10.1099/mic.0.032029-0 (2009).
14 Finkelshtein, A., Roth, D., Ben Jacob, E. & Ingham, C. J. Bacterial swarms recruit cargo bacteria to pave the way in toxic environments. mBio 6, e00074-00015, doi:10.1128/mBio.00074-15 (2015).
15 Morales-Soto, N. et al. Preparation, imaging, and quantification of bacterial surface motility assays. Journal of visualized experiments: JoVE, doi:10.3791/52338 (2015).
16 Lambert, G., Vyawahare, S. & Austin, R. H. Bacteria and game theory: the rise and fall of cooperation in spatially heterogeneous environments. Interface focus 4, 20140029, doi:10.1098/rsfs.2014.0029 (2014).
17 Schultz, D., Wolynes, P. G., Ben Jacob, E. & Onuchic, J. N. Deciding fate in adverse times: sporulation and competence in Bacillus subtilis. Proceedings of the National Academy of Sciences of the United States of America 106, 21027-21034, doi:10.1073/pnas.0912185106 (2009).
18 Venkatesh, M. et al. Symbiotic bacterial metabolites regulate gastrointestinal barrier function via the xenobiotic sensor PXR and Toll-like receptor 4. Immunity 41, 296-310, doi:10.1016/j.immuni.2014.06.014 (2014).
19 Jeffers, M. et al. A novel human fibroblast growth factor treats experimental intestinal inflammation. Gastroenterology 123, 1151-1162 (2002).
20 Kearns, D B, and R Losick. Swarming motility in undomesticated Bacillus subtilis. Mol Microbiol 49: 581-590 (2003).
21 Kearns, D B, F Chu, R Rudner, and R Losick. Genes governing in Bacillus subtilis and evidence for a phase variation mechanism controlling surface motility. Mol Microbiol 52: 357-369 (2004).
22 Singh V, Yeoh B S, Carvalho F, Gewirtz A T, Vijay-Kumar M. Proneness of TLR5 deficient mice to develop colitis is microbiota dependent. Gut Microbes Jul. 4; 6(4):279-83 (2015).
23 Van De Walle J, Hendrickx A, Romier B, Larondelle Y, Schneider Y J. Inflammatory parameters in Caco2 cells: effect of stimuli nature, concentration, combination and cell differentiation. Toxicol In Vitro August; 24(5):1441-9 (2010).

What is claimed is:
1. A method of isolating a single bacterial strain from a complex bacterial mix in a fecal material, the method comprising
isolating bacterial hyperswarmers as a single bacterial strain from the fecal material on a plate agar assay under aerobic conditions to provide isolated bacterial hyperswarmers; and
propagating the isolated bacterial hyperswarmers in culture to isolate a single bacterial strain.
2. The method of claim 1, wherein the fecal material is from an animal model of inflammation or from an animal with an intestinal inflammation.
3. The method of claim 2, wherein the animal is a human.
4. The method of claim 3, wherein the human has irritable bowel disease.
5. The method of claim 2, wherein the animal is a farm animal.

* * * * *